US010596148B2

(12) United States Patent
Merary et al.

(10) Patent No.: US 10,596,148 B2
(45) Date of Patent: Mar. 24, 2020

(54) TOPICAL COMPOSITIONS FOR TREATMENT OF PSORIASIS

(71) Applicant: Prestigio Ltd., Yahud (IL)

(72) Inventors: David Merary, Yahud (IL); Iris Raveh, Yahud (IL)

(73) Assignee: Prestigio Ltd., Yahud (IL)

( * ) Notice: Subject to any disclaimer, the term of this patent is extended or adjusted under 35 U.S.C. 154(b) by 70 days.

(21) Appl. No.: 15/756,723

(22) PCT Filed: Aug. 30, 2016

(86) PCT No.: PCT/IB2016/001317
§ 371 (c)(1),
(2) Date: Mar. 1, 2018

(87) PCT Pub. No.: WO2017/037534
PCT Pub. Date: Mar. 9, 2017

(65) Prior Publication Data

US 2019/0054062 A1 Feb. 21, 2019

Related U.S. Application Data

(60) Provisional application No. 62/214,987, filed on Sep. 6, 2015.

(51) Int. Cl.

| | |
|---|---|
| ***A61K 36/00*** | (2006.01) |
| ***A61K 31/355*** | (2006.01) |
| ***A61K 47/06*** | (2006.01) |
| ***A61K 9/06*** | (2006.01) |
| ***A61K 31/045*** | (2006.01) |
| ***A61K 31/07*** | (2006.01) |
| ***A61K 31/60*** | (2006.01) |
| ***A61K 33/30*** | (2006.01) |
| ***A61P 17/06*** | (2006.01) |
| ***A61K 9/00*** | (2006.01) |
| ***A61K 36/537*** | (2006.01) |
| ***A61K 36/736*** | (2006.01) |
| ***A61K 36/76*** | (2006.01) |
| ***A61K 47/26*** | (2006.01) |
| ***A61K 47/44*** | (2017.01) |
| ***A61K 8/27*** | (2006.01) |
| ***A61K 8/34*** | (2006.01) |
| ***A61K 8/368*** | (2006.01) |
| ***A61K 8/67*** | (2006.01) |
| ***A61Q 19/00*** | (2006.01) |
| ***A61K 8/92*** | (2006.01) |
| ***A61K 8/9789*** | (2017.01) |

(52) U.S. Cl.
CPC .............. *A61K 31/355* (2013.01); *A61K 8/27* (2013.01); *A61K 8/34* (2013.01); *A61K 8/368* (2013.01); *A61K 8/671* (2013.01); *A61K 8/678* (2013.01); *A61K 8/922* (2013.01); *A61K 8/9789* (2017.08); *A61K 9/0014* (2013.01); *A61K 9/06* (2013.01); *A61K 31/045* (2013.01); *A61K 31/07* (2013.01); *A61K 31/60* (2013.01); *A61K 33/30* (2013.01); *A61K 36/537* (2013.01); *A61K 36/736* (2013.01); *A61K 36/76* (2013.01); *A61K 47/06* (2013.01); *A61K 47/26* (2013.01); *A61K 47/44* (2013.01); *A61P 17/06* (2018.01); *A61Q 19/00* (2013.01)

(58) Field of Classification Search
CPC ...................................................... A61K 36/00
USPC ......................................................... 424/725
See application file for complete search history.

(56) References Cited

U.S. PATENT DOCUMENTS

| | | | |
|---|---|---|---|
| 6,599,513 | B2 | 7/2003 | Deckers et al. |
| 8,845,600 | B2 | 9/2014 | Webb |
| 8,933,257 | B2 | 1/2015 | Swanzy |
| 2015/0224049 | A1 | 8/2015 | Florence et al. |

OTHER PUBLICATIONS

International Search Report in International Application No. PCT/IB2016/001317 dated Jan. 27, 2017.

*Primary Examiner* — Michael V Meller
(74) *Attorney, Agent, or Firm* — Greenberg Traurig, LLP

(57) ABSTRACT

The present invention provides safe and effective topical compositions for the treatment of psoriasis and alleviation and prevention of frequent recurrence of psoriasis symptoms as well as treatment of seborrheic dermatitis. The compositions comprise therapeutically effective amounts of salicylic acid, zinc oxide, bisabolol, at least one pharmaceutically acceptable carrier selected from the group comprising white petrolatum, lanolin, propylene glycol, and combinations thereof, herbal oils selected from the group comprising Salvia Hispanica seed oil, evening primrose oil, grape seed oil, Nigella seed oil, Silybum Marianum oil, Primus Amygdalus Dulcis (sweet almond) oil, borage oil, Lavendula Angustifolia (lavender) oil, Cannabis sativa seed oil and mixtures thereof and other pharmaceutically acceptable ingredients. Unlike many topical compositions for the treatment of these skin afflictions, the compositions of the instant invention do not contain steroids (like cortisone) or coal tar. They are hypoallergenic and essentially free of side-effects.

10 Claims, 14 Drawing Sheets

Example 1 - Pictures of the psoriasis lesions before, during and after the treatment with DermaZor ointment

Before Using DermaZor Ointment– Week 0

After 2 Weeks – Week 2

Before Using DermaZor Ointment – Week 0

After Two Weeks – Week 2

Before using DermaZor Oint.– Week 0

After Two Weeks – Week 2

Symptoms alleviation during treatment

Symptoms alleviation during treatment

TOPICAL COMPOSITIONS FOR TREATMENT OF PSORIASIS

CROSS REFERENCE TO RELATED APPLICATIONS

This application is a U.S. national phase application under 35 U.S.C. 371 of PCT International Application No. PCT/IB2016/001317, filed on Aug. 30, 2016 which claims priority to U.S. Provisional Patent Application Ser. No. 62/214,987, filed on Sep. 6, 2015, the entire contents of each of which are hereby incorporated by reference in their entirety.

FIELD OF THE INVENTION

The present invention discloses safe and effective topical compositions for the treatment of psoriasis and alleviation and prevention of frequent recurrence of psoriasis symptoms as well as treatment of seborrheic dermatitis.

BACKGROUND

Psoriasis is one of the most prevalent autoimmune diseases, characterized by patches of abnormal skin. The affected skin patches are red, present scales and are itchy and irritated.

There are five main types of psoriasis: plaque, Guttate, inverse, pustular and erythrodermic. Plaque psoriasis is the most common.

A large proportion of psoriatic people develop psoriatic arthritis, affecting the joints and tendons.

Seborrheic dermatitis is an inflammatory skin disorder affecting the scalp, face and torso. It is a chronic, relapsing dermatitis.

SUMMARY

This invention provides safe and effective topical compositions for the treatment of psoriasis and seborrheic dermatitis.

Unlike many topical compositions for the treatment of these skin afflictions, the compositions of the instant invention do not contain steroids (like cortisone) or coal tar. They are hypoallergenic and essentially free of side-effects.

The compositions of this invention are very effective in alleviating the symptoms of psoriasis, including the red patches associated with it, as well as the symptoms of seborrheic dermatitis.

Methods of treatment of psoriasis and seborrheic dermatitis are described.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DETAILED DESCRIPTION

Figure 1:
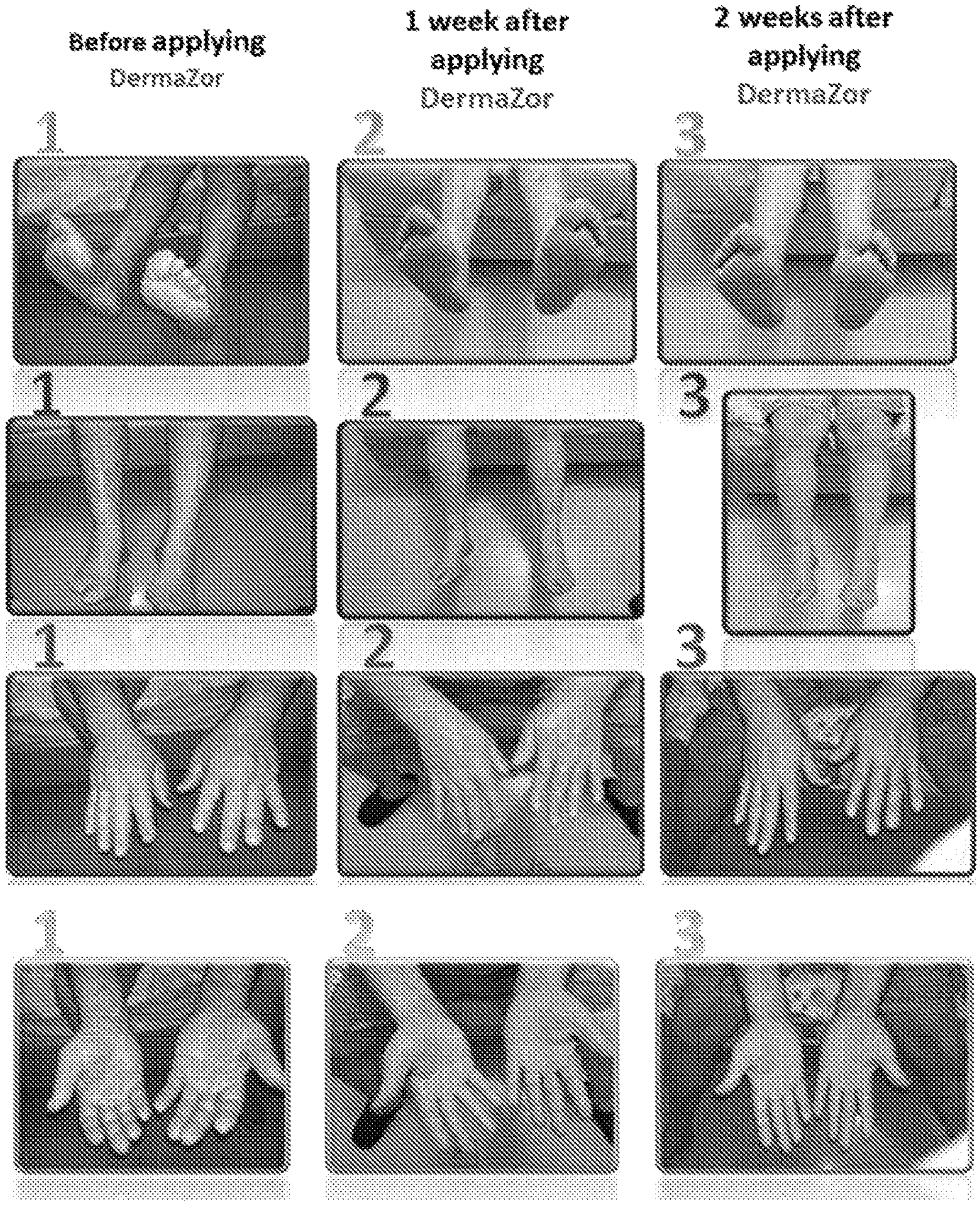
FIG. 1 depicts pictures of the psoriasis lesions of the patient in Example 1 before, during and after the treatment.
Figure 2A:
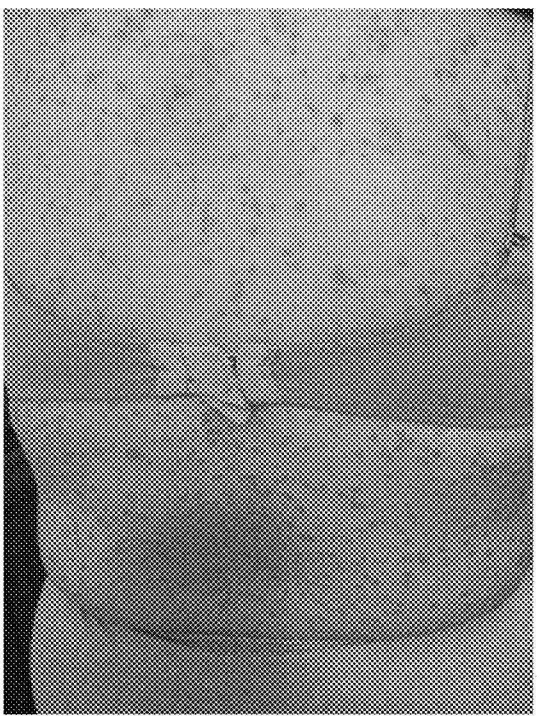
FIGS. 2A-2L depict pictures of the psoriasis lesions of the patient in Example 2 before, during and after the treatment.
Figure 2B:
Figure 2C:
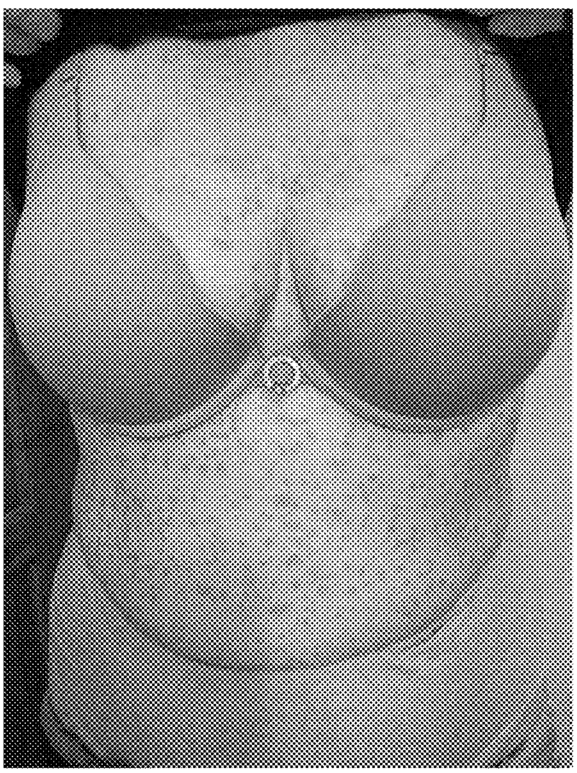
Figure 2D:
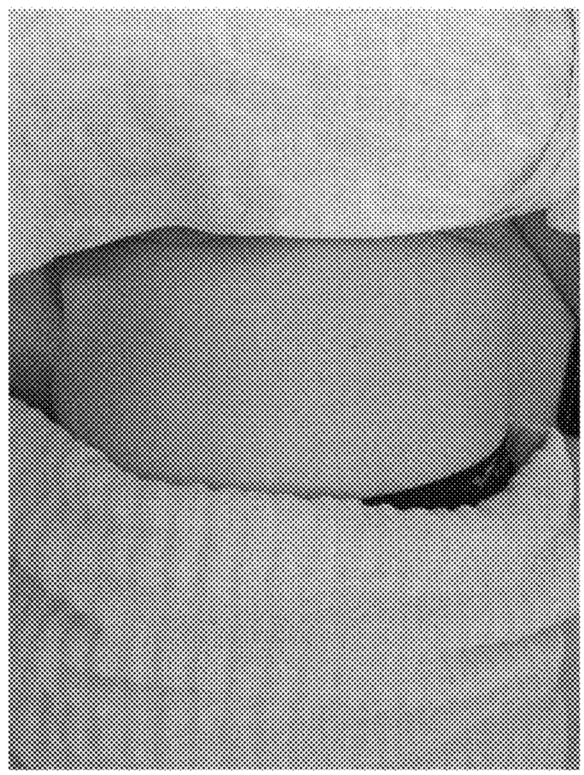
Figure 2E:
Figure 2F:
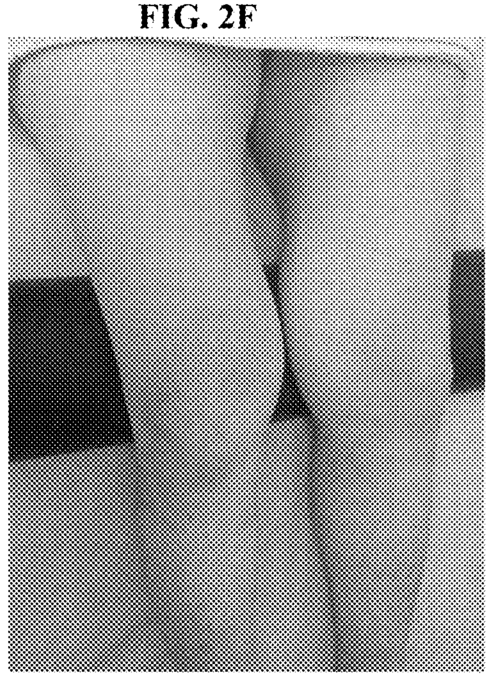
Figure 2G:
Figure 2H:
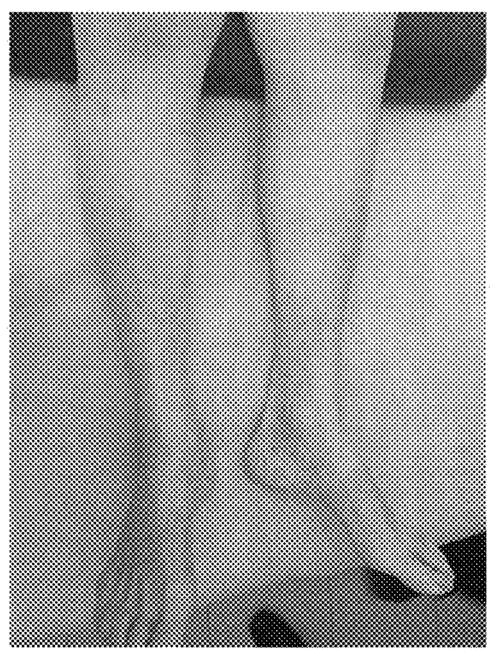
Figure 2I:
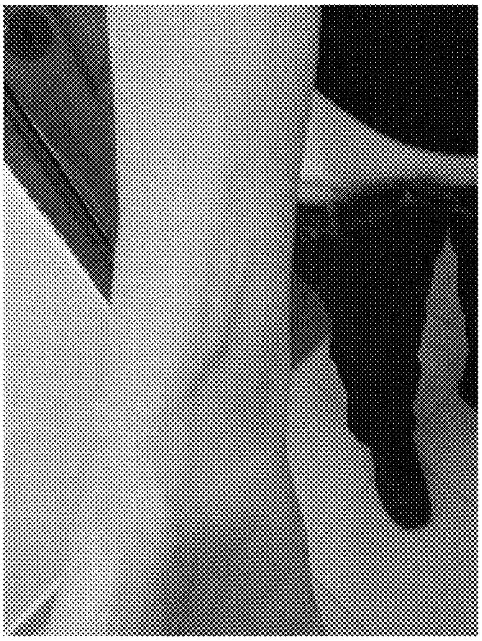
Figure 2J:
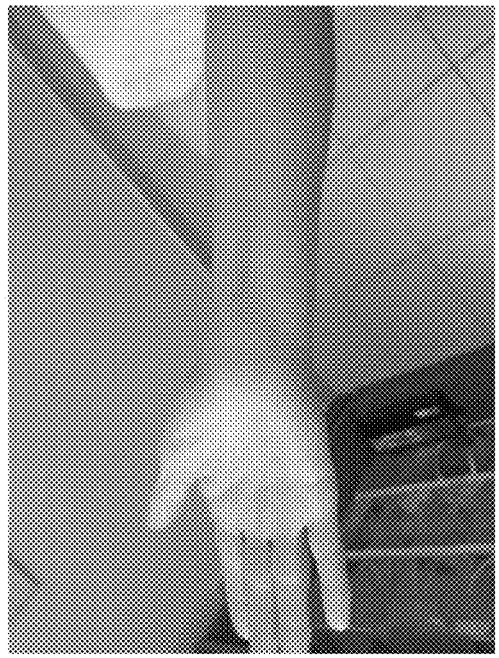
Figure 2K:
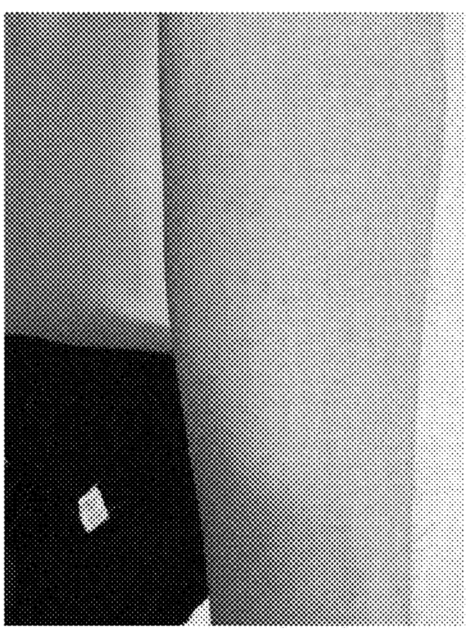
Figure 2L:
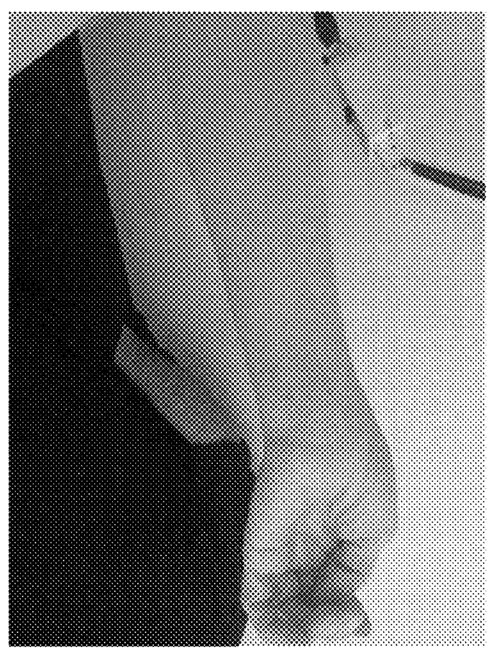
Figure 3A:
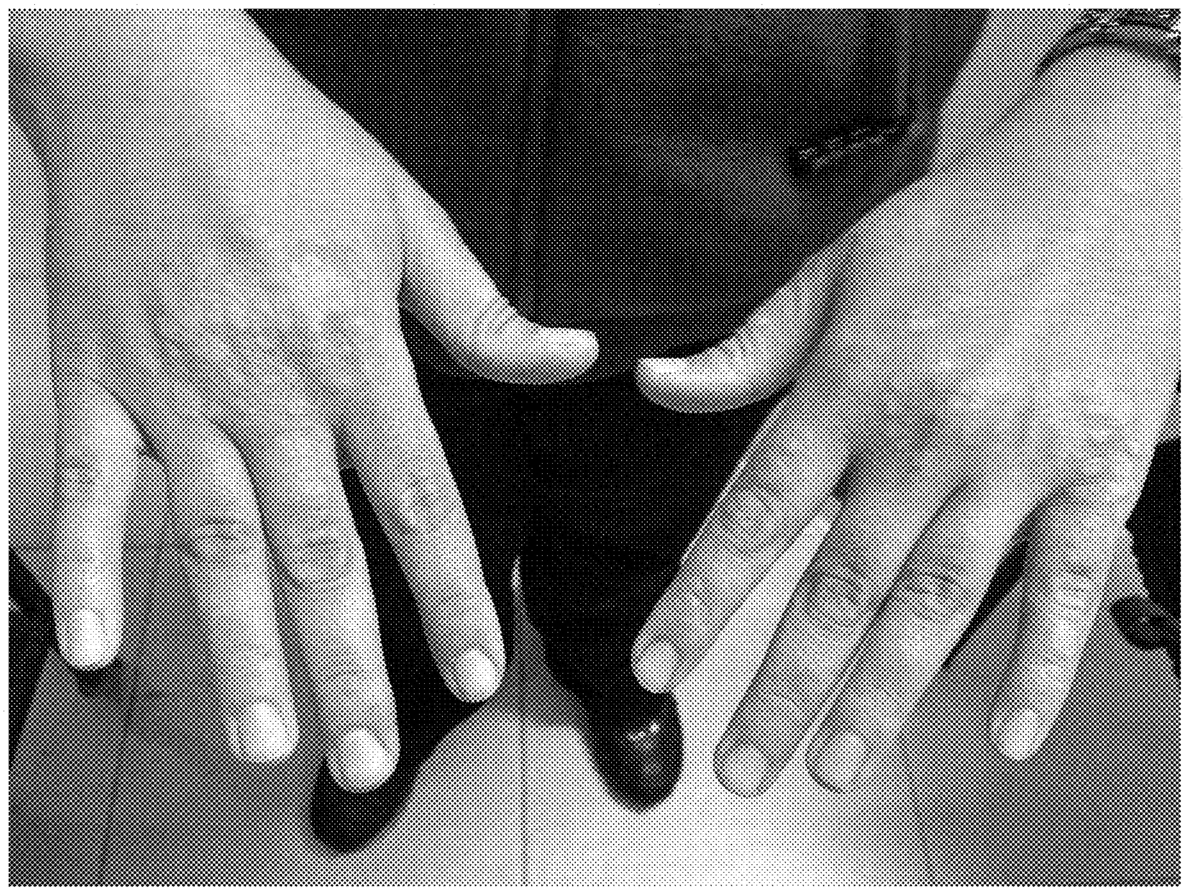
FIGS. 3A-3F depicts pictures of the psoriasis lesions of the patient in Example 3 before, during and after the treatment.
Figure 3B:
Figure 3C:
Figure 3D:
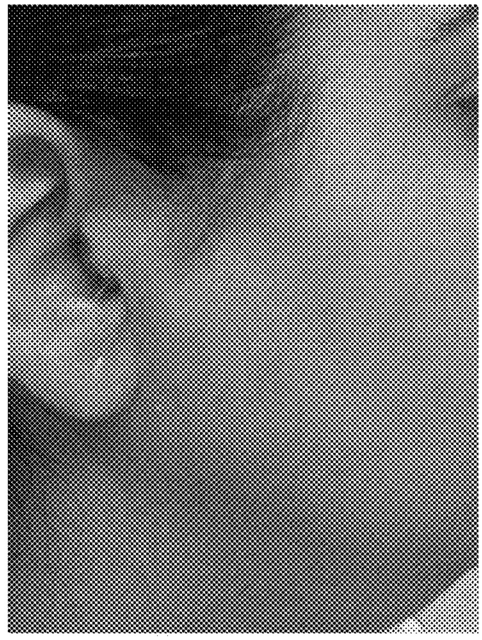
Figure 3E:
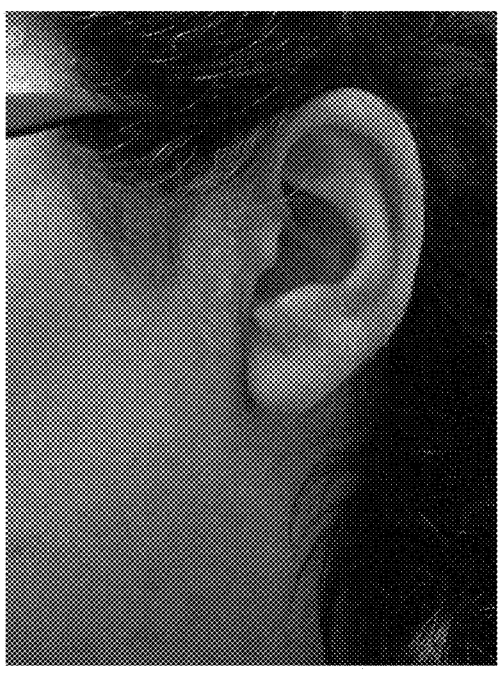
Figure 3F:
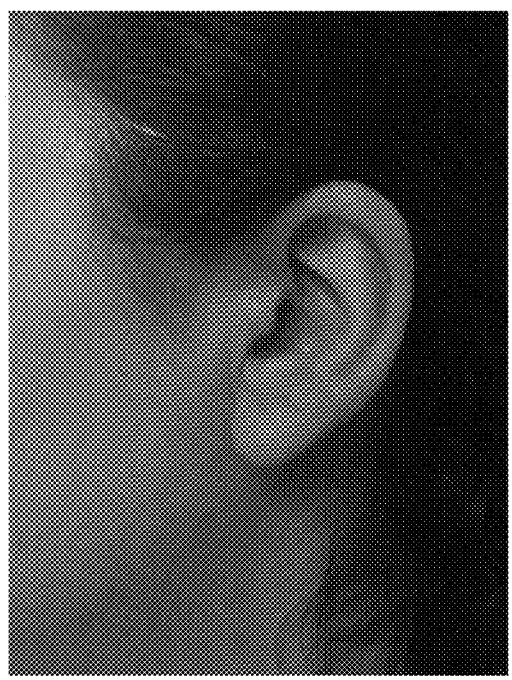

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases “in one embodiment” and “in some embodiments” as used herein do not necessarily refer to the same embodiment(s), though it may. Furthermore, the phrases “in another embodiment” and “in some other embodiments” as used herein do not necessarily refer to a different embodiment, although it may. Thus, as described below, various embodiments of the invention may be readily combined, without departing from the scope or spirit of the invention.

In addition, as used herein, the term “or” is an inclusive “or” operator, and is equivalent to the term “and/or,” unless the context clearly dictates otherwise. The term “based on” is not exclusive and allows for being based on additional factors not described, unless the context clearly dictates otherwise. In addition, throughout the specification, the meaning of “a,” “an,” and “the” include plural references. The meaning of “in” includes “in” and “on.”

This invention provides topical compositions for the treatment of psoriasis and prevention of its frequent recurrence and treatment of seborrheic dermatitis.

In some embodiments, the ingredients of the compositions of this invention comprise therapeutically effective amounts of salicylic acid and zinc oxide, at least one pharmaceutically acceptable carrier selected from the group consisting of petrolatum, white petrolatum jelly, lanolin, mineral oil, propylene glycol, polyethylene glycol, shea butter, propoleum (propolis) and combinations thereof, an least one herbal oil selected from the group comprising bisabolol, Salvia Hispanica seed oil, evening primrose oil, grape seed oil, Nigella seed oil, Silybum Marianum oil, Prunus Amygdalus Dulcis (sweet almond oil), borage oil, Lavendula Angustifolia (lavender) oil and mixtures thereof, and other pharmaceutically acceptable ingredients.

In some embodiments, the other pharmaceutically acceptable ingredients include, but are not limited to, polysorbate 80, phenoxyethanol, corn starch, polyethylene-20-sorbitan tristearate, propylene glycol, cyclomethicone, elastomer blend, purified water and mixtures thereof.

In some embodiments, the compositions are formulated in the dosage form of an ointment, a cream, a lotion, a foam or a spray.

Without intending to be limited to any particular theory, the ointment dosage form is effective in the treatment of psoriasis, due to its occlusive effect, which is beneficial for promoting the healing of psoriasis lesions.

In some embodiments, topical ointment compositions comprising 1-5% w/w salicylic acid, 5-12% w/w zinc oxide, 0.1-2% w/w bisabolol, 10-20% w/w propylene glycol and other pharmaceutically acceptable ingredients were effective in the treatment of psoriasis.

In some embodiments, topical ointment compositions comprising 1-5% w/w salicylic acid, 5-12% w/w zinc oxide, 0.1-2% w/w bisabolol, 10-20% w/w propylene glycol, 10-20% w/w white petrolatum, 10-15% w/w lanolin, 5-10% w/w Salvia Hispanica seed oil, 3-7% w/w grape seed oil, 3-7% w/w White Willow oil, 3-7% w/w evening primrose oil, 3-7% w/w silicone elastomer blend and other pharmaceutically acceptable ingredients performed well in clinical tests.

The inventors surprisingly found that compositions comprised of a mixture of carefully selected ingredients in well balanced concentrations are very effective in treating psoriasis, or preventing its frequent recurrence or alleviating its symptoms, or combinations thereof.

In an embodiment, there is provided a topical composition for the treatment of psoriasis, or the alleviation of psoriasis, or the prevention of frequent recurrence of psoriasis symptoms, comprising therapeutically effective amounts of 2-4% w/w salicylic acid, 8-10% w/w zinc oxide, 10-15% w/w white petrolatum, 10-14% w/w lanolin, 4-6% w/w grape seed oil, 4-6% w/w Calendula Officinalis flower oil, 4-6% w/w evening primrose oil, 2-4% w/w beeswax, 0.5-3% w/w Nigella seed oil, 1-3% w/w calamine, 0.5-3% Silybum Marianum seed oil, 0.5-2% w/w Vitamin A or its palmitate, 0.5-2% w/w Vitamin E or its acetate, 0.5-2% w/w borage oil, 0.5-2% w/w sweet almond oil, 0.5-2% w/w bisabolol, 0.1-0.3% w/w lavender oil, additional herbal oils selected from the group consisting of 0-7% w/w Salvia Hispanica seed oil, 0-5% w/w White Willow oil, 0-5% w/w Linum Usitatissimum seed oil, 0-5% w/w Anthemis Nobilis flower oil, 0-6% w/w Cannabis Sativa seed oil, and mixtures thereof and pharmaceutically acceptable ingredients selected from the group consisting of 0-3% w/w polysorbate 80, 0-2% w/w phenoxyethanol, 0-10% w/w corn starch, 0-3% w/w polyethylene-20-sorbitan tristearate, 0-16% w/w propylene glycol. 0-3% w/w cyclomethicone, 0-6% w/w elastomer blend, 0-12% w/w purified water and mixtures thereof.

In some embodiments, the composition is effective in the treatment, prevention, or alleviation of seborrheic dermatitis.

In another embodiment, there is provided a topical ointment composition comprising 1-5% w/w salicylic acid, 10-20% w/w white petrolatum, 10-20% w/w propylene glycol, 10-15% w/w lanolin, 5-12% w/w zinc oxide, 5-10% w/w Salvia Hispanica seed oil, 3-7% w/w grape seed oil, 3-7% w/w White Willow oil, 2-10% w/w Calendula Officinalis flower oil, 3-7% w/w evening primrose oil, 3-7% w/w silicone elastomer blend, 2-5% w/w beeswax, 1-5% w/w cyclomethicone, 1-3% w/w Nigella seed oil, 1-3% w/w calamine, 0.5-2% w/w Silybum Marianum seed oil, 0.5-2% w/w Vitamin A, 0.5-2% w/w Vitamin E, 0.5-2% w/w borage oil, 0.5-2% w/w sweet almond oil (Prunus Amygdalis Dulcis) 0.1-2% w/w bisabolol (Dragosantol 100), 0.1-0.3 w/w lavender oil (Lavandula Angustifolia).

In another embodiment, there is provided a topical ointment composition (see Example 4) consisting of 3% w/w salicylic acid, 14.8% w/w white petrolatum, 13.5% w/w propylene glycol, 12% w/w lanolin, 9% w/w zinc oxide, 7% w/w Salvia Hispanica seed oil, 5% w/w grape seed oil, 5% w/w White Willow oil, 5% w/w Calendula Officinalis flower oil, 5% w/w evening primrose oil, 5% w/w silicone elastomer blend, 3% w/w beeswax, 2.5% w/w cyclomethicone, 2% w/w Nigella seed oil, 2% calamine, 1% w/w Silybum Marianum seed oil, 1% w/w Vitamin A, 1% w/w Vitamin E, 1% w/w borage oil, 1% w/w sweet almond oil (Prunus Amygdalis Dulcis) 1% w/w bisabolol (Dragosantol 100), 0.2% w/w lavender oil (Lavandula Angustifolia).

While the ointment compositions of the instant invention do not have to comprise a preservative, said compositions are stable to microbial growth.

Side-effects of said compositions of this invention are mild, if at all present.

The present invention provides a method of treatment of psoriasis and psoriasis symptoms in a patient in need thereof, by topical application of therapeutically effective doses of the topical compositions of the instant invention to a skin area affected by psoriasis for one to 14 days, 1-3 times daily until the psoriasis symptoms alleviate and repeating the treatment as needed.

In some embodiments, the compositions are applied to the skin once per day. In some embodiments, the compositions are applied to the skin twice per day. In some embodiments, the compositions are applied three times per day.

In some embodiments, the compositions are applied for up to 14 days. In some embodiments, the compositions are applied for up to 13 days. In some embodiments, the compositions are applied for up to 12 days. In some embodiments, the compositions are applied for up to 11 days. In some embodiments, the compositions are applied for up to 10 days. In some embodiments, the compositions are applied for up to 9 days. In some embodiments, the compositions are applied for up to 8 days. In some embodiments, the compositions are applied for up to 7 days. In some embodiments, the compositions are applied for up to 6 days. In some embodiments, the compositions are applied for up to 5 days. In some embodiments, the compositions are applied for up to 4 days. In some embodiments, the compositions are applied for up to 3 days. In some embodiments, the compositions are applied for up to 2 days. In some embodiments, the compositions are applied for 1 day.

In some embodiments, the above method of treatment is effective for psoriasis of the type selected from the group consisting of plaque psoriasis, nail psoriasis, scalp psoriasis, Guttate psoriasis, inverse psoriasis, pustular psoriasis, erythrodermic psoriasis and psoriatic arthritis.

The above method of treatment is effective in treating and alleviating at least one of the psoriasis symptoms selected from the group comprising scaling, dry cracked skin, bleeding, flaking, irritation, itching, burning, soreness, swollen and stiff joints, red patches of skin and combinations thereof.

Surprisingly, said methods of treatment are effective in alleviating not only the above psoriasis symptoms but also the psoriasis-associated skin redness.

In addition, the compositions of the instant invention are effective also in the treatment of seborrheic dermatitis by topical application of therapeutically effective doses of the topical compositions of the instant invention to a skin area affected by seborrheic dermatitis for one to 14 days, 1-3 times daily until the symptoms alleviate and repeating the treatment as needed.

In some embodiments, the compositions are applied to the skin once per day. In some embodiments, the compositions are applied to the skin twice per day. In some embodiments, the compositions are applied three times per day.

In some embodiments, the compositions are applied for up to 14 days. In some embodiments, the compositions are applied for up to 13 days. In some embodiments, the compositions are applied for up to 12 days. In some embodiments, the compositions are applied for up to 11 days. In some embodiments, the compositions are applied for up to 10 days. In some embodiments, the compositions are applied for up to 9 days. In some embodiments, the compositions are applied for up to 8 days. In some embodiments, the compositions are applied for up to 7 days. In some embodiments, the compositions are applied for up to 6 days. In some embodiments, the compositions are applied for up to 5 days. In some embodiments, the compositions are applied for up to 4 days. In some embodiments, the compositions are applied for up to 3 days. In some embodiments, the compositions are applied for up to 2 days. In some embodiments, the compositions are applied for 1 day.

Examples 1-3 describe in detail three of the psoriasis cases treated with the ointment composition of the present invention (referred to as DermaZor ointment, see Example 4).

The alleviation of the psoriasis symptoms during the treatment is detailed in Tables 1-3.

In all these cases the patients experienced a dramatic and fast healing of the psoriasis lesions. Pictures of the psoriasis lesions of the patients before, during and after the treatment with DermaZor ointment (FIGS. 1-3) exemplify the effectivity of the psoriasis treatment.

In an embodiment, there are provided topical compositions for the treatment of psoriasis, prevention of frequent recurrence, or alleviation of psoriasis symptoms, comprising therapeutically effective amounts of salicylic acid, zinc oxide, bisabolol, at least one pharmaceutically acceptable carrier selected from the group comprising petrolatum, white petrolatum jelly, lanolin, mineral oil, propylene glycol, polyethylene glycol, water, shea butter, propoleum (propolis) and combinations thereof, at least one herbal oil selected from the group comprising Salvia Hispanica seed oil, evening primrose oil, grape seed oil, Nigella seed oil, Silybum Marianum oil, Prunus Amygdalus Dulcis (sweet almond) oil, borage oil, Lavendula Angustifolia (lavender) oil, Cannabis sativa oil, Linum Usitassimum seed oil, Anthemis Nobilis flower oil, and mixtures thereof, and other pharmaceutically acceptable ingredients selected from the group consisting of corn starch, polysorbate 80, polyoxyethylene-20-sorbitan tristearate, phenoxyethanol and mixtures thereof.

In some embodiments, the above compositions may further comprise at least one pharmaceutically acceptable ingredient selected from the group comprising calamine, beeswax, cyclomethicone, silicone elastomer blend, vitamin A, vitamin E and mixtures thereof.

In an embodiment, there are provided topical ointment compositions comprising 1-5% w/w salicylic acid, 5-12% w/w zinc oxide, 0.1-2% w/w bisabolol, 10-20% w/w propylene glycol and other pharmaceutically acceptable ingredients.

In another embodiment, there are provided topical ointment compositions comprising 1-5% w/w salicylic acid, 5-12% w/w zinc oxide, 0.1-2% w/w bisabolol, 10-20% w/w propylene glycol, 10-20% w/w white petrolatum, 10-15% w/w lanolin, 5-10% w/w Salvia Hispanica seed oil, 3-7% w/w grape seed oil, 3-7% w/w White Willow oil, 3-7% w/w evening primrose oil, 3-7% w/w silicone elastomer blend and other pharmaceutically acceptable ingredients.

In some embodiments, the topical compositions of the instant invention are formulated in the dosage form of an ointment, a cream, a lotion, a foam or a spray.

In an embodiment, the ointment composition of the instant invention is in the form of a stable, essentially waterless ointment. The above composition is stable although it does not have to contain an added preservative.

In another embodiment, the composition of the instant invention is in the form of a stable topical cream.

In an embodiment, there is provided a topical cream composition comprising 1-5% w/w salicylic acid, 10-15% w/w lanolin, 5-15% w/w white petrolatum, 5-15% w/w purified water, 5-15% w/w zinc oxide, 6-10% w/w corn starch, 2-8% w/w grape seed oil, 2-8% w/w Cannabis sativa oil, 2-8% w/w Calendula Officinalis oil, 2-8% w/w Linum Usitassimum seed oil, 2-8% w/w Anthemis Nobilis flower oil, 2-8% w/w evening primrose oil, 2-4% w/w beeswax, 1-3% w/w polyoxyethylene-20-sorbitan tristearate, 1-3% w/w polysorbate 80, 1-3% w/w Silybum Marianum seed oil, 1-3% w/w calamine, 0.5-2% w/w phenoxyethanol, 0.5-2% w/w Vitamin A palmitate, 0.5-2% w/w Vitamin E acetate, 0.5-2% w/w Borago Officinalis seed oil, 0.5-2% w/w sweet almond oil, 0.5-2% w/w Nigella seed oil, 0.1-0.3 w/w lavender (Lavandula Angustifolia) oil.

In another embodiment, there is provided a topical cream composition (see Example 5) consisting of 3% w/w salicylic acid, 12% w/w lanolin, 10% w/w white petrolatum, 9.8% w/w purified water, 9% w/w zinc oxide, 8% w/w corn starch, 5% w/w grape seed oil, 5% w/w Cannabis Sativa oil, 5% w/w Calendula Officinalis oil, 5% w/w Linum Usitassimum seed oil, 5% w/w Anthemis Nobilis flower oil, 5% w/w evening primrose oil, 3% w/w beeswax, 2% w/w polyoxyethylene-20-sorbitan tristearate, 2% w/w polysorbate 80, 2% w/w Silybum Marianum seed oil, 2% w/w calamine, 1% w/w phenoxyethanol, 1% w/w Vitamin A palmitate, 1% w/w Vitamin E acetate, 1% w/w Borago Officinalis seed oil, 1% w/w sweet almond oil, 1% w/w Nigella seed oil and 0.3 w/w lavender (Lavandula Angustifolia) oil.

In an embodiment, the salicylic acid which is a component of the compositions of the instant invention is essentially in solubilized form. In another embodiment, the salicylic acid which is a component of the compositions of the instant invention is partly in solubilized form and partly in suspended form.

In an embodiment, there is provided a method of treatment of psoriasis and/or psoriasis symptoms in a patient in need thereof, by topical application of therapeutically effective doses of the topical compositions of the instant invention to a skin area affected by psoriasis for one to 14 days, 1-3 times daily until the psoriasis symptoms alleviate and repeating the treatment as needed.

In some embodiments, the compositions are applied to the skin once per day. In some embodiments, the compositions are applied to the skin twice per day. In some embodiments, the compositions are applied three times per day.

In some embodiments, the compositions are applied for up to 14 days. In some embodiments, the compositions are applied for up to 13 days. In some embodiments, the compositions are applied for up to 12 days. In some embodiments, the compositions are applied for up to 11 days. In some embodiments, the compositions are applied for up to 10 days. In some embodiments, the compositions are applied for up to 9 days. In some embodiments, the compositions are applied for up to 8 days. In some embodiments, the compositions are applied for up to 7 days. In some embodiments, the compositions are applied for up to 6 days. In some embodiments, the compositions are applied for up to 5 days. In some embodiments, the compositions are applied for up to 4 days. In some embodiments, the compositions are applied for up to 3 days. In some embodiments, the compositions are applied for up to 2 days. In some embodiments, the compositions are applied for 1 day.

In another embodiment, the above method of treatment is effective for psoriasis of the type selected from the group comprising plaque psoriasis, nail psoriasis, scalp psoriasis, Guttate psoriasis, inverse psoriasis, pustular psoriasis, erythrodermic psoriasis and psoriatic arthritis.

In an embodiment, there is provided a method of treatment effective in treating and alleviating at least one of the psoriasis symptoms selected from the group comprising scaling, dry cracked skin, bleeding, flaking, irritation, itching, burning, soreness, swollen and stiff joints, red patches of skin and combinations thereof.

In another embodiment, said methods of treatment are effective in alleviating not only the above psoriasis symptoms but also the psoriasis-associated skin redness.

In yet another embodiment, there is provided a kit comprising 1-12 units of one of the dosage forms of this invention and instructions for use.

EXAMPLES

The following examples illustrate certain embodiments of the invention but are not meant to limit the scope of the claims in any way. The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, percentages are weight per weight, molecular weight is weight average molecular weight, temperature is in degrees Centigrade, and pressure is at or near atmospheric.

Example 1—Treatment of Psoriasis Vulgaris with DermaZor Ointment

A male patient aged 54 suffered from very severe psoriasis vulgaris for 5 years. The cause of the disease is believed to be result of trauma and stress. His 25 old daughter suffered from psoriasis as well. Affected body area percentage at the beginning of the treatment was 20-25%.

| Psoriasis Area | 0 (Absent), 1 (Slight), 2 (Moderate), 3 (Severe), 4 (Very Severe) |
|---|---|
| Armpit | Severe |
| Arms | Very Severe |
| Elbows | Severe |
| Hands | Severe |
| Nails | Severe |
| Knees | Very Severe |
| Legs | Very Severe |
| Feet | Very Severe |

| Treatment | |
|---|---|
| The extent to which the patient followed treatment guideline | High |
| Level of Use | Very good |
| General Feeling | Very good |
| Skin Improvement | Very good |
| Side Effects | No |
| Continuing Care | For another 8 months |

TABLE 1

| Symptoms alleviation during treatment | | | | | | | |
|---|---|---|---|---|---|---|---|
| Symptoms | week 0 | week 1 | week 2 | week 3 | week 4 | week 5 | week 6 |
| Itching and scratching | 4 | 2 | 1 | 0.5 | 0.1 | 0 | 0 |
| Erythema | 4 | 2.5 | 1.5 | 1 | 0.5 | 0 | 0 |
| Scales | 4 | 2 | 1 | 0.5 | 0.1 | 0 | 0 |
| Thickness | 4 | 2 | 1 | 0.5 | 0.1 | 0 | 0 |

Figure 4:
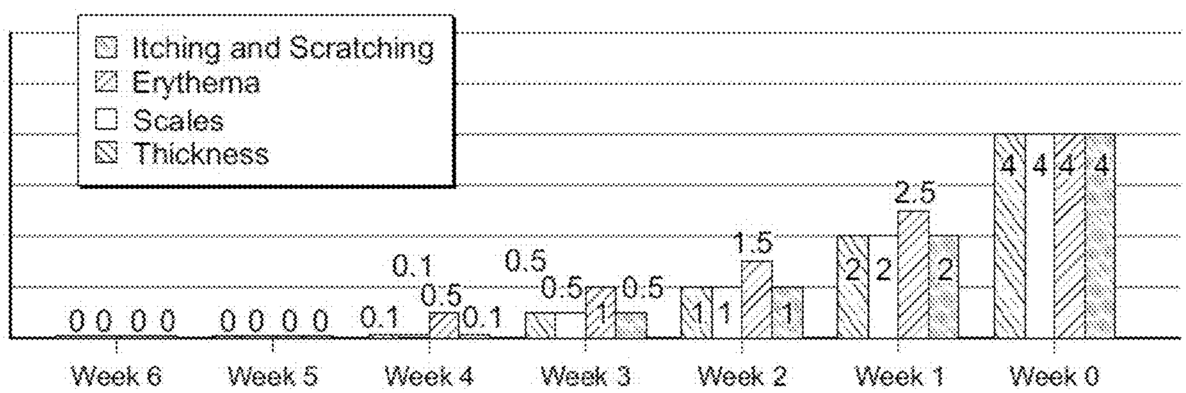
FIG. 4 is a chart showing the symptoms alleviation during treatment of the patient in Example 1.

FIG. 4 shows the symptoms alleviation during treatment.

Figure 5:
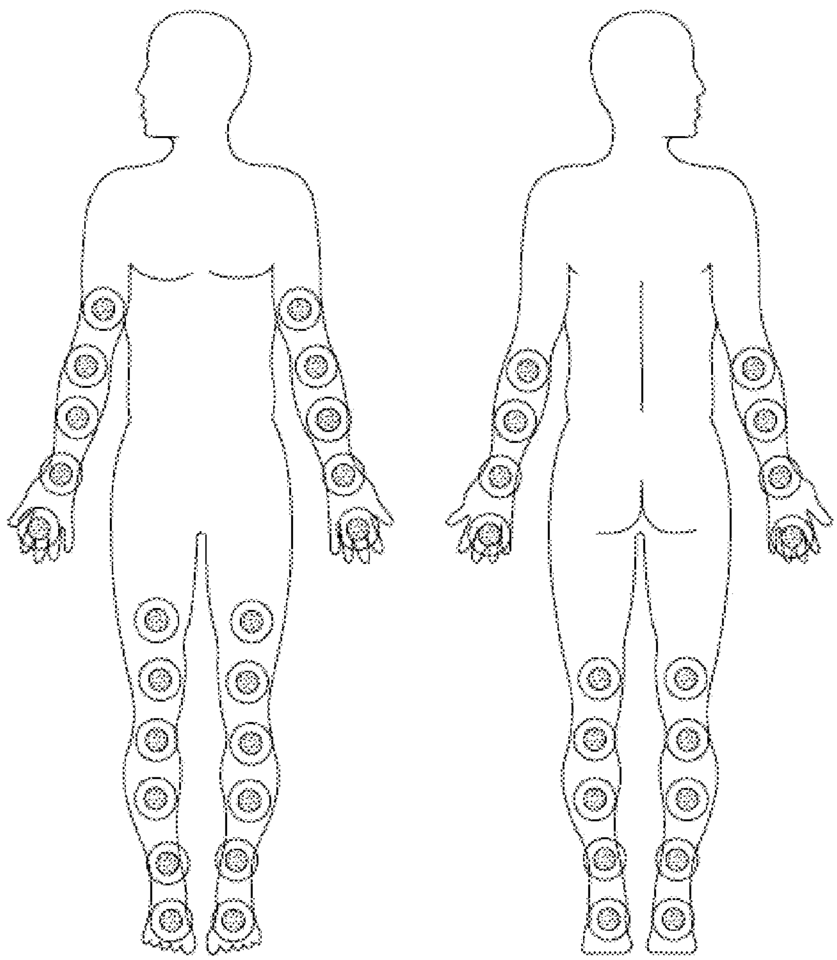
FIG. 5 shows the location of psoriasis lesions on the body of the patient in Example 1.

FIG. 5 shows the location of psoriasis lesions on the body.

Example 2—Treatment of Guttate Psoriasis with DermaZor Ointment

A female patient aged 65 suffered from very severe Guttate psoriasis for many years. The affected body area percentage was 80% and the cause of the disease was unknown. No genetic factors were known.

| Psoriasis Area | 0 (Absent), 1 (Slight), 2 (Moderate), 3 (Severe), 4 (Very Severe) |
|---|---|
| Chest | Very Severe |
| Stomach | Very Severe |
| Trunk | Very Severe |
| Arms | Severe |
| Elbows | Severe |
| Hands | Severe |
| Nails | Severe |
| Upper Back | Very Severe |
| Lower Back | Very Severe |
| Buttock | Very Severe |
| Thigh | Very Severe |
| Knees | Very Severe |
| Legs | Very Severe |
| Feet | Severe |

| Treatment | |
|---|---|
| The extent to which the patient followed treatment guideline | Good |
| Level of Use | Very High |
| General Feeling | Very Good |
| Skin Improvement | Dramatic |
| Side Effects | No |
| Continuing Care | Not for now |

Figure 6:
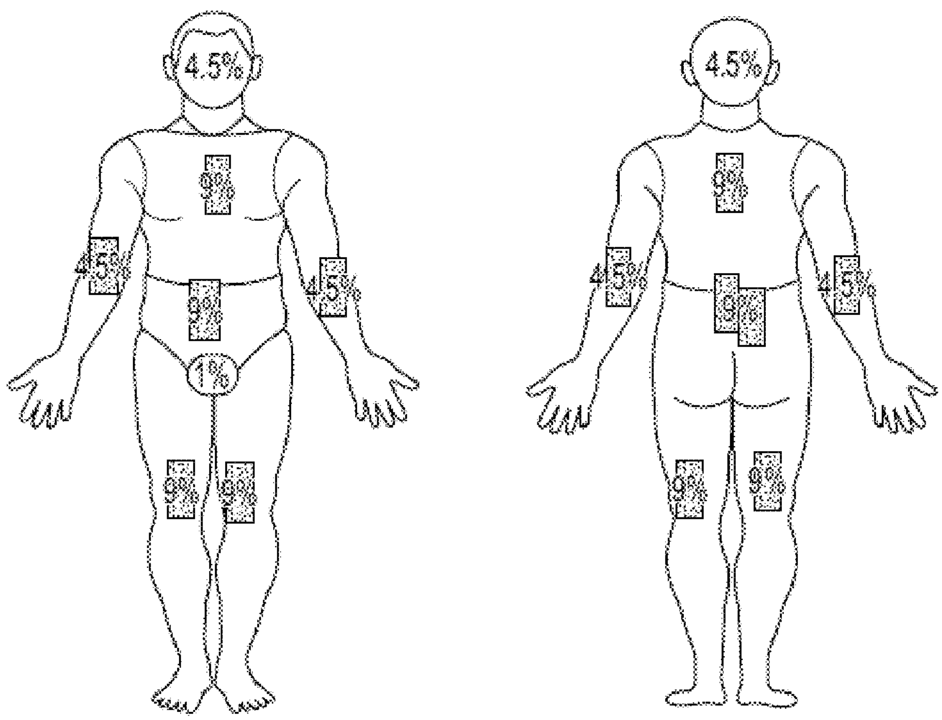
FIG. 6 shows the percentage of psoriasis affected body areas of the patient in Example 2.

FIG. 6 shows the percentage of psoriasis affected body areas.

TABLE 2

| Symptoms alleviation during treatment | | | | | | | |
|---|---|---|---|---|---|---|---|
| Symptoms | week 0 | week 1 | week 2 | week 3 | week 4 | week 5 | week 6 |
| Itching/scratching | 4.5 | 0.4 | 0 | 0 | 0 | 0 | 0 |
| Erythema | 4.5 | 2 | 0.5 | 0 | 0 | 0 | 0 |
| Scales | 0 | 0 | 0 | 0 | 0 | 0 | 0 |
| Thickness | 0 | 0 | 0 | 0 | 0 | 0 | 0 |

Figure 7:
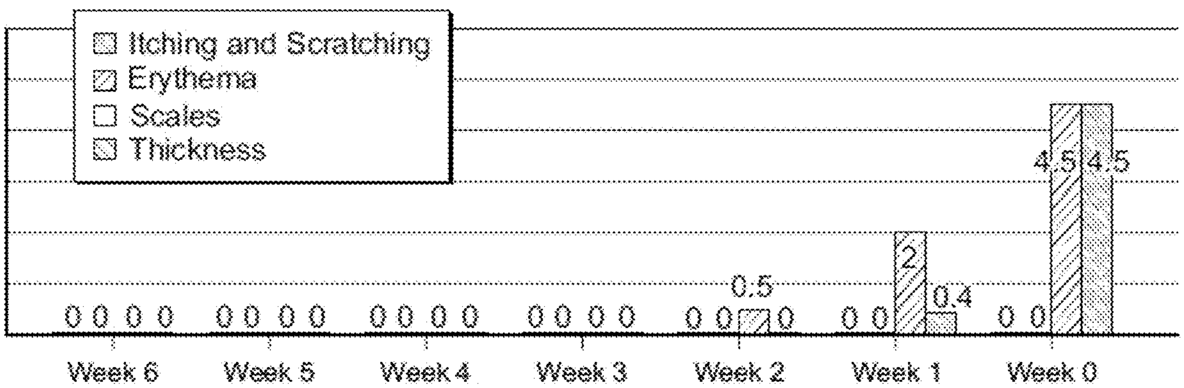
FIG. 7 shows the alleviation during treatment of the patient in Example 2.

FIG. 7 shows the symptoms alleviation during treatment.

Figure 8:
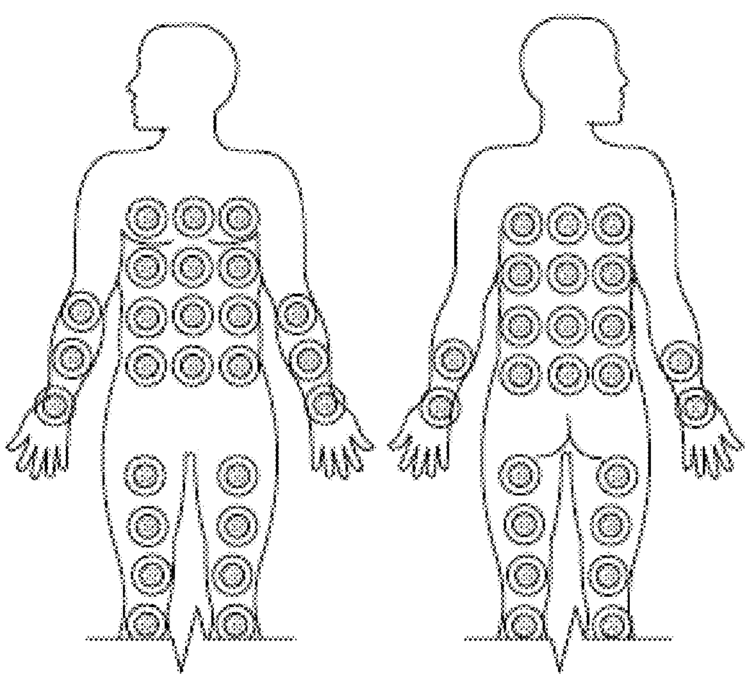
FIG. 8 shows the location of psoriasis lesions on the body of the patient in Example 2.

FIG. 8 shows the location of psoriasis lesions on the body.

Example 3—Treatment of Psoriasis Vulgaris (60% Area) with DermaZor Ointment

A female patient aged 38 suffered from very severe psoriasis vulgaris for many years. The affected body area percentage was 60% all over the body, but especially on the face and ears.

| Psoriasis Area | 0 (Absent), 1 (Slight), 2 (Moderate), 3 (Severe), 4 (Very Severe) |
|---|---|
| Armpit | Very Severe |
| Arms | Very Severe |
| Elbows | Very Severe |
| Hands | Very Severe |
| Nails | Very Severe |
| Knees | Very Severe |
| Legs | Very Severe |
| Feet | Very Severe |

| Treatment | |
|---|---|
| The extent to which the patient followed treatment guideline | High |
| Level of Use | High |
| General Feeling | Very good |
| Skin Improvement | Dramatic |
| Side Effects | No |
| Continuing Care | There was a big improvement in a short period of time. She applied a lot of ointment. |

Figure 9:
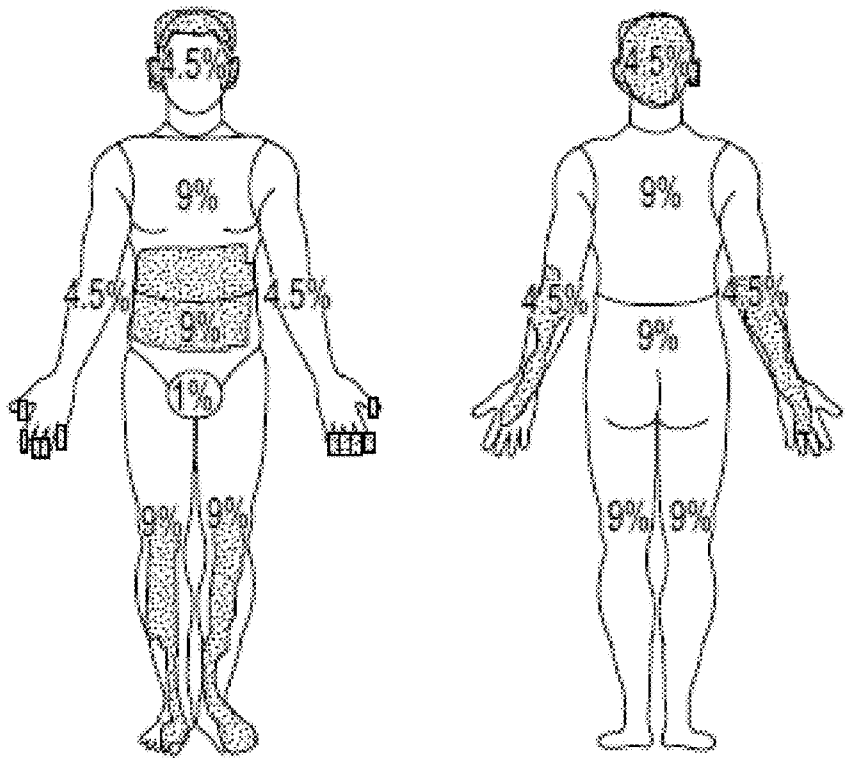
FIG. 9 shows the percentage of psoriasis affected body areas of the patient in Example 3.

FIG. 9 shows the percentage of psoriasis affected body areas.

TABLE 3

| Symptoms alleviation during treatment | | | | | | | |
|---|---|---|---|---|---|---|---|
| Symptoms | week 0 | week 1 | week 2 | week 3 | week 4 | week 5 | week 6 |
| Itching and scratching | 4.5 | 0.5 | 0 | 0 | 0 | 0 | 0 |
| Erythema | 4.5 | 2.3 | 1 | 0 | 0 | 0 | 0 |
| Scales | 4.5 | 1 | 0 | 0 | 0 | 0 | 0 |
| Thickness | 4.5 | 1 | 0 | 0 | 0 | 0 | 0 |

Figure 10:
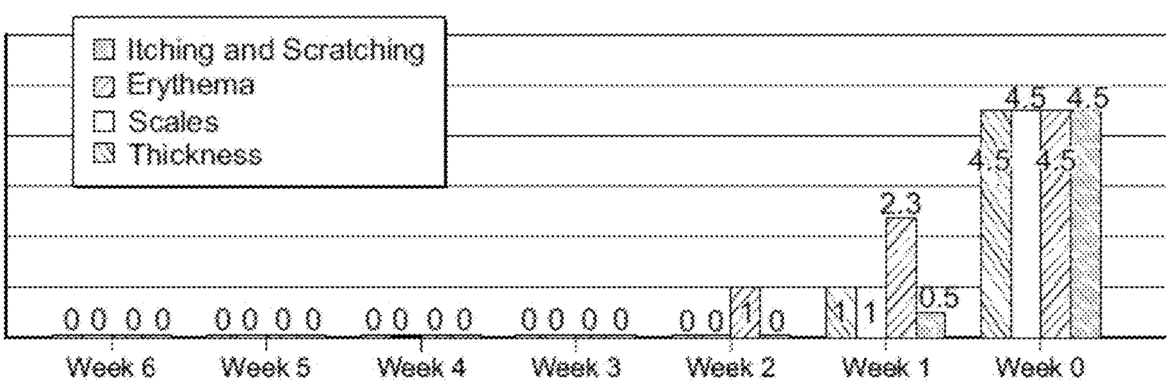
FIG. 10 shows the symptoms alleviation during treatment of the patient in Example 3.

FIG. 10 shows the symptoms alleviation during treatment.

Figure 11:
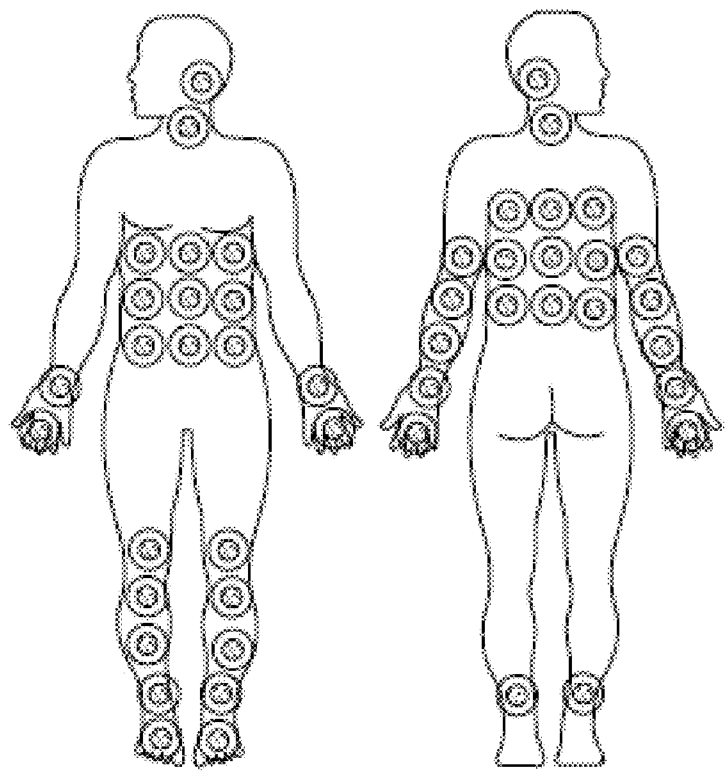
FIG. 11 shows the location of psoriasis lesions on the body of the patient in Example 3.

FIG. 11 shows the location of psoriasis lesions on the body.

Example 4—DermaZor Ointment

| Ingredient | % w/w |
|---|---|
| Salicylic acid | 3.0 |
| White Petrolatum | 14.8 |
| Propylene Glycol | 13.5 |
| Lanolin | 12.0 |
| Zinc Oxide | 9.0 |
| *Salvia Hispanica* seed oil (Omega 3 Oil) | 7.0 |
| Grape seed Oil | 5.0 |
| White Willow Oil | 5.0 |
| *Calendula Officinalis* Flower Oil | 5.0 |
| Evening Primrose Oil (*Oenothera Biennis*) | 5.0 |
| Elastomer Bland 9045 | 5.0 |
| Beeswax | 3.0 |
| Cyclomethicone | 2.5 |
| Nigella Seed Oil | 2.0 |
| Calamine | 2.0 |
| Silybum Marianum Seed Oil | 1.0 |
| Vitamin A | 1.0 |
| Vitamin E | 1.0 |
| Borage Oil | 1.0 |
| *Prunus Amygdalus Dulcis* (Sweet Almond) Oil | 1.0 |
| Dragosantol 100 - (Bisabolol) | 1.0 |
| *Lavandula Angustifolia* (Lavender) Oil | 0.2 |
| Total | 100.0 |

Example 5—DermaZor Cream

| Ingredient | % w/w |
|---|---|
| Salicylic Acid | 3.0 |
| Lanolin | 12.0 |
| White petrolatum | 10.0 |
| Purified Water | 9.8 |
| Zinc Oxide | 9.0 |
| *Zea Mays* (Corn) Starch | 8.0 |
| *Vitis Vinifera* (Grape) Seed Oil | 5.0 |
| *Cannabis Sativa* Seed Oil | 5.0 |
| *Calendula Officinalis* Flower Oil | 5.0 |
| *Linum Usitatissimum* Seed Oil | 5.0 |
| *Anthemis Nobilis* Flower Oil | 5.0 |
| *Oenothera Biennis* (Evening Primrose Oil) | 5.0 |
| Beeswax | 3.0 |
| Polyoxyethylene-20-sorbitan tristearate | 2.0 |
| Polysorbate 80 | 2.0 |
| Silybum Marianum Seed Oil | 2.0 |
| Calamine | 2.0 |
| Phenoxyethanol | 1.0 |
| Retinyl Palmitate (Vitamin A palmitate) | 1.0 |
| Tocopheryl Acetate (Vitamin E acetate) | 1.0 |
| *Borago Officinalis* seed oil | 1.0 |
| *Prunus Amygdalus Dulcis* (Sweet Almond Oil) | 1.0 |
| Bisabolol | 1.0 |
| Nigella Seed Oil | 1.0 |
| *Lavandula angustifolia* oil | 0.2 |
| Total | 100.0% |

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. An ointment for the treatment of psoriasis in a human consisting essentially of 1-5% w/w salicylic acid, 10-20% w/w white petrolatum, 10-20% w/w propylene glycol, 10-15% w/w lanolin, 5-12% w/w zinc oxide, 5-10% w/w Salvia Hispanica seed oil, 3-7% w/w grape seed oil, 3-7% w/w White Willow oil, 2-10% w/w Calendula Officinalis flower oil, 3-7% w/w Evening Primrose oil, 3-7% w/w silicone elastomer blend, 2-5% w/w beeswax, 1-5% w/w cyclomethicone, 1-3% w/w Nigella seed oil, 1-3% w/w calamine, 0.5-2% w/w Silybum Marianum seed oil, 0.5-2% w/w Vitamin A, 0.5-2% w/w Vitamin E, 0.5-2% w/w borage oil, 0.5-2% w/w sweet almond oil, 0.1-2% w/w bisabolol and 0.1-0.3% w/w lavender oil.

2. A cream for the treatment of psoriasis in a human consisting essentially of 1-5% w/w salicylic acid, 10-15% w/w lanolin, 5-15% w/w white petrolatum, 5-15% w/w purified water, 5-15% w/w zinc oxide, 6-10% w/w corn starch, 2-8% w/w grape seed oil, 2-8% w/w Cannabis sativa oil, 2-8% w/w Calendula Officinalis oil, 2-8% w/w Linum Usitassimum seed oil, 2-8% w/w Anthemis Nobilis flower oil, 2-8% w/w Evening Primrose oil, 2-4% w/w beeswax, 1-3% w/w polyoxyethylene-20-sorbitan tristearate, 1-3% w/w polysorbate 80, 1-3% w/w Silybum Marianum seed oil, 1-3% w/w calamine, 0.5-2% w/w phenoxyethanol, 0.5-2% w/w Vitamin A palmitate, 0.5-2% w/w Vitamin E acetate, 0.5-2% w/w Borago Officinalis seed oil, 0.5-2% w/w sweet almond oil, 0.5-2% w/w Nigella seed oil and 0.1-0.3% w/w lavender oil.

3. A method of treatment of psoriasis and alleviation of psoriasis symptoms in the human in need thereof, consisting essentially of applying topically a therapeutically effective dose of the ointment of claim 1 to a skin area affected by psoriasis for one to 14 days, 1-3 times daily, until at least one psoriasis symptom alleviate; and repeating the treatment as needed.

4. The method of treatment of claim 3, wherein the psoriasis is of the type selected from the group consisting of plaque psoriasis, nail psoriasis, scalp psoriasis, Guttate psoriasis, inverse psoriasis, pustular psoriasis, erythrodermic psoriasis and psoriatic arthritis.

5. The method of treatment of claim 3, wherein the at least one psoriasis symptom is selected from the group consisting of scaling, dry cracked skin, bleeding, flaking, irritation, itching, burning, soreness, swollen and stiff joints, red patches of skin and combinations thereof.

6. The method of treatment of claim 3, wherein the ointment is effective in alleviating psoriasis-associated skin redness and at least one of scaling, dry cracked skin, bleeding, flaking, irritation, itching, burning, soreness, swollen and stiff joints, or red patches of skin.

7. A method of treatment of psoriasis and alleviation of psoriasis symptoms in the human in need thereof, consisting essentially of applying topically a therapeutically effective dose of the cream of claim 2 to a skin area affected by psoriasis for one to 14 days, 1-3 times daily, until at least one psoriasis symptom alleviate; and repeating the treatment as needed.

8. The method of treatment of claim 7, wherein the psoriasis is of the type selected from the group consisting of plaque psoriasis, nail psoriasis, scalp psoriasis, Guttate psoriasis, inverse psoriasis, pustular psoriasis, erythrodermic psoriasis and psoriatic arthritis.

9. The method of treatment of claim 7, wherein the at least one psoriasis symptom is selected from the group consisting of scaling, dry cracked skin, bleeding, flaking, irritation, itching, burning, soreness, swollen and stiff joints, red patches of skin and combinations thereof.

10. The method of treatment of claim 7, wherein the cream is effective in alleviating psoriasis-associated skin redness and at least one of scaling, dry cracked skin, bleeding, flaking, irritation, itching, burning, soreness, swollen and stiff joints, or red patches of skin.

* * * * *